United States Patent
Kangas et al.

(10) Patent No.: US 11,981,629 B2
(45) Date of Patent: *May 14, 2024

(54) METHOD FOR REDUCING HEAVY END FORMATION AND CATALYST LOSS IN A HYDROFORMYLATION PROCESS

(71) Applicant: PERSTORP AB, Perstorp (SD)

(72) Inventors: Matias Kangas, Helsingborg (SE); Stefan Nilsson, Munka-Ljungby (SE)

(73) Assignee: PERSTORP AB, Perstorp (SE)

( * ) Notice: Subject to any disclaimer, the term of this patent is extended or adjusted under 35 U.S.C. 154(b) by 255 days.

This patent is subject to a terminal disclaimer.

(21) Appl. No.: 17/624,862

(22) PCT Filed: Jun. 23, 2020

(86) PCT No.: PCT/SE2020/050650
§ 371 (c)(1),
(2) Date: Jan. 5, 2022

(87) PCT Pub. No.: WO2021/006795
PCT Pub. Date: Jan. 14, 2021

(65) Prior Publication Data
US 2022/0251015 A1    Aug. 11, 2022

(30) Foreign Application Priority Data

Jul. 5, 2019  (SE) .................................... 1930237-1
Jul. 18, 2019  (SE) .................................... 1930249-6

(51) Int. Cl.
B01D 3/14    (2006.01)
B01D 3/42    (2006.01)
(Continued)

(52) U.S. Cl.
CPC .............. *C07C 45/86* (2013.01); *B01D 3/148* (2013.01); *B01D 3/42* (2013.01); *B01J 31/185* (2013.01);
(Continued)

(58) Field of Classification Search
CPC . B01D 3/148; B01D 3/42; C07C 45/86; B01J 31/185
See application file for complete search history.

(56) References Cited

U.S. PATENT DOCUMENTS 4,151,209 A * 4/1979 Paul ........................ C07C 45/50
568/454
4,760,194 A * 7/1988 Phillips ................... C07C 45/49
502/166

(Continued)

FOREIGN PATENT DOCUMENTS

EP    0404193 A1    12/1990
EP    2900373 A1    8/2015
(Continued)

OTHER PUBLICATIONS

International Search Report and Written Opinion dated Jul. 13, 2020 for corresponding PCT Application No. PCT/SE2020/050650.

*Primary Examiner* — Jonathan Miller
(74) *Attorney, Agent, or Firm* — POLSINELLI PC

(57) ABSTRACT

The present invention refers to a method for reducing heavy end formation and catalyst loss in a continuous hydroformylation process, where an olefin or an olefin mixture is reacted with carbon monoxide and hydrogen in a reactor assembly (1) in the presence of a rhodium complex catalyst, comprising at least one organobisphosphite ligand, in order to produce an aldehyde. Said method comprising the addition of an epoxide to the reaction mixture and the continuous or discontinuous removal of early heavy ends.

20 Claims, 6 Drawing Sheets

(51) Int. Cl.
    *B01J 31/18* (2006.01)
    *C07C 45/86* (2006.01)
(52) U.S. Cl.
    CPC .... *B01J 2231/321* (2013.01); *B01J 2531/822* (2013.01)

(56) References Cited

U.S. PATENT DOCUMENTS

| | | | | |
|---|---|---|---|---|
| 5,364,950 | A | * | 11/1994 | Babin .................. C07C 45/50 568/429 |
| 5,672,766 | A | * | 9/1997 | Mori ................... C07C 45/50 568/454 |
| 5,763,671 | A | * | 6/1998 | Bryant ................. C07F 9/025 568/454 |
| 6,153,800 | A | * | 11/2000 | Gelling ............... C07F 9/145 568/454 |
| 6,610,891 | B1 | * | 8/2003 | O'Young ............. B01J 31/185 568/454 |
| 8,907,129 | B2 | * | 12/2014 | Grass .................. C07C 45/50 562/512.2 |
| 2004/0054236 | A1 | * | 3/2004 | Ueda .................. C07C 45/50 568/451 |
| 2007/0282132 | A1 | * | 12/2007 | Beadle ................ C07C 45/50 568/451 |
| 2012/0172630 | A1 | | 7/2012 | Liu |
| 2016/0257635 | A1 | | 9/2016 | Eisenschmid et al. |
| 2017/0233322 | A1 | | 8/2017 | Miller et al. |

FOREIGN PATENT DOCUMENTS

| | | |
|---|---|---|
| GB | 2192182 A | 1/1988 |
| JP | H08165266 A | 6/1996 |

* cited by examiner

METHOD FOR REDUCING HEAVY END FORMATION AND CATALYST LOSS IN A HYDROFORMYLATION PROCESS

CROSS-REFERENCE TO RELATED APPLICATIONS

This application is a national stage application (under 35 U.S.C. § 371) of PCT/SE2020/050650, filed Jun. 23, 2020, which claims benefit of Swedish Application Nos. 1930237-1, filed Jul. 5, 2019, and 1930249-6, filed Jul. 18, 2019, which are incorporated herein by reference in their entireties.

FIELD OF THE INVENTION

The present invention refers to a method for reducing heavy end formation and catalyst loss in a continuous hydroformylation process, where an olefin or an olefin mixture is reacted with carbon monoxide and hydrogen in a reactor assembly (1) in the presence of a rhodium complex catalyst, comprising at least one organobisphosphite ligand, in order to produce an aldehyde. Said method comprising the addition of an epoxide to the reaction mixture and the continuous or discontinuous removal of early heavy ends.

BACKGROUND ART

Hydroformylation, also called the oxo process, is an important industrial process that generates aldehydes by reacting olefins with carbon monoxide and hydrogen in the presence of transition metal catalyst complexes. It is well known that preferred processes involve continuous hydroformylation and recycling of a catalyst solution containing a metal-organophosphorus ligand complex catalyst wherein the metal is a Group VIII transition metal, preferably rhodium. Such art is exemplified by for instance U.S. Pat. Nos. 4,148,830, 4,717,775, and 4,769,498. Yielded aldehydes have a wide range of utility, for example, as intermediates for hydrogenation to aliphatic alcohols, so called oxo alcohols, for amination to aliphatic amines, for oxidation to aliphatic acids, and for aldol condensation to produce components of plasticizers.

Rhodium catalysts need ligands for stabilizing and/or activating the rhodium in rhodium-catalyzed low-pressure hydroformylation. Rhodium complexed with phosphorus ligands, wherein the phosphorus ligands typically are organophosphines and/or organophosphites, are well known in the art. Rhodium-bisphosphite catalysts are known to be used in the hydroformylation of linear olefins, like propenes, butenes and hexenes and they have an effect of increased activity and selectivity to unbranched reaction products.

Hydroformylation is often accompanied by a series of parallel and secondary reactions. Due to their high reactivity the formed aldehydes undergo aldol condensation reactions, Tischenko reactions and acetalization reactions and produce high-boiling by-products, such as dimers, trimers and tetramers. These high-boiling by-products produced during the hydroformylation process are called heavy ends and they can cause a lot of problems to the process, since their accumulation can lead to a forced bleeding of rhodium and ligand containing solution. Heavy ends formation can take place in reactors, as well as in hot places like distillation bottoms.

The condensation reaction producing heavy ends is generating water and when heavy ends are formed to a large extent, there is consequently a large amount of water produced in the hydroformylation process. Water formed in the aldol condensation reaction in the reaction mixture causes the organobisphosphite ligand to undergo hydrolysis. When the phosphite ligand undergo hydrolysis, acidic decomposition products are formed, e.g. hydroxyalkylphosphonic acids, that catalyzes many of the reactions forming heavy ends, which in turn, produces additional water, causing further hydrolysis of the ligand. This autocatalytic reaction leads to a substantial amount of high boiling compounds in the process and a significant loss of phosphite ligand resulting in unnecessary high ligand costs.

A far more challenging problem than accelerated ligand decomposition is the accumulation of high-boiling compounds in the process. The concentration of heavy ends in the reaction mixture increases with time and heavy ends have to actively be removed from the process. Accumulation of heavy ends is troublesome since they take up space in the process and can affect both the yield and the selectivity of the hydroformylation products. There has to be a balance between the rate of removal and the rate of formation of heavy ends. If the heavy ends increase too much the useful capacity and effectiveness of the hydroformylation system is reduced and a catalyst change is required. Replacing the catalyst is a costly procedure, not only because of the very expensive catalyst and free and complexed ligand, but also because the reaction has to be stopped. The accumulation of heavy ends may also cause clogging in the reactor system, if not inhibited in time, causing a lot of process problems and reaction stops.

Accordingly, it is important to limit the amount of heavy ends accumulating in the reaction mixture and to prevent the formation of heavy ends during the hydroformylation reaction. The amount of heavy ends can to a certain extent be reduced via optimized reaction parameters, catalyst concentration and the use of solvents. But heavy ends still have to actively be removed from the reaction mixture in order to avoid accumulation in the reactor. It is not possible to separate the more high-boiling heavy ends from the reaction solution by distillation, since the phosphite ligand thermally decomposes at high temperatures. It is generally required to bleed the complex heavy ends from the system. The bleed does unfortunately not only contain heavy ends, but also e.g., smaller amount of the aldehyde product, the rhodium-phosphite complex catalyst, free phosphite ligand, organic solvent, unreacted olefin and dissolved carbon monoxide and hydrogen. Since the phosphite ligand decompose at high temperatures, it is impossible to separate the rhodium-phosphite complex catalyst from the more high-boiling heavy ends and recycle back to the hydroformylation reaction without losing the valuable ligand.

Rhodium is a highly expensive catalyst that is recycled in the hydroformylation reaction. The loss of rhodium due to heavy ends removal is very costly. Heavy ends accumulation is therefore a serious process problem, often leading to a forced rhodium bleed. Reducing the formation of heavy ends, is a way to reduce the rhodium loss, because of the subsequently reduced amount of heavy ends removed from the process.

There is also another problem with rhodium catalysts comprising phosphite ligands, they lose catalytic activity over time during continuous use in a hydroformylation reaction. Some decomposition products of the phosphite ligands can coordinate with rhodium and form complexes that are less reactive than rhodium-phosphite complex catalysts. These phosphite ligand decomposition products act as catalyst poisons or inhibitors, and lower the catalyst activity of rhodium-phosphite complex catalysts. If the ligand degradation caused by water from heavy ends formation were reduced, the hydroformylation process could be run for an extended period of time before the catalyst solution had to be exchanged.

Due to the tendency of phosphite ligands to undergo hydrolysis, alcoholysis and/or transesterification, under customary hydroformylation conditions, there is a lot of prior art relating to methods of stabilization of phosphite ligands in hydroformylation. There is however not many publications focusing on the amount of heavy ends and how to effectively reduce the amount of heavy ends formed in a hydroformylation reaction.

There are several publications on methods for stabilizing catalyst and/or organophosphite ligands using different kinds of amines. For instance EP3126319, disclosing a method where a water soluble amine is used instead of aqueous buffer solution to neutralize any phosphoric acidic compound. U.S. Pat. No. 4,567,306 discloses a method to decrease degradation of cyclic phosphite ligands by adding a tertiary amine. Tertiary amines reduce ligand destruction by neutralizing the acidic materials and forming ammonium salts. However, many amines also catalyze the undesirable condensation of the aldehyde products, thus leading to increased formation of undesirable by-products, i.e. heavy ends.

WO2019083700 discloses a process to reduce heavy end formation in a hydroformylation reaction by the addition of a certain class of nitrogen compounds. Many nitrogen compounds are however associated with environmental and health concerns. WO2010003073 discloses a two-stage process of hydroformylation and product-catalyst separation for controlling heavy ends in a catalyst recycle stream. This method does only partly controls the amount of heavy ends and is associated with addition equipment, process redesign and a risk of ligand loss.

EP455261 discloses a process for producing a 1,3-diol and/or a 3-hydroxyaldehyde by hydroformylation of an epoxide using a rhodium-containing catalyst. In this European patent application the epoxide is used a reactant, not as an additive, and there is no disclosure of decreasing the amount of heavy ends by using an epoxide. EP0590611, is focusing on stabilizing phosphite ligands against degradation by the addition of an epoxide. The patent is however silent on heavy ends complications and what effect an epoxide may have on the amount of heavy ends in a continuous hydroformylation process.

Accordingly, there is a need for an efficient way to reduce the amount of heavy ends formed in a continuous hydroformylation process and consequently increase the stability of the organophosphite ligand by decreased hydrolysis. There is also a need to limit the amount of high-boiling heavy ends in order to reduce the loss of rhodium catalyst.

DESCRIPTION OF THE INVENTION

It has surprisingly been found that by adding small amounts of an epoxide to a hydroformylation mixture, the amount of heavy ends produced during the hydroformylation process can be drastically reduced. This efficient way of limiting the formation of heavy ends and thus preventing heavy ends from accumulating in the reaction mixture, has also a stabilizing effect on the organobisphosphite ligand of a rhodium complex catalyst in a hydroformylation reaction.

The method of the present invention is further a very efficient way of reducing catalyst loss by limiting the formation of more complex heavy ends, in which the epoxide addition is combined with a continuous or discontinuous removal of early heavy ends.

Figure 1:
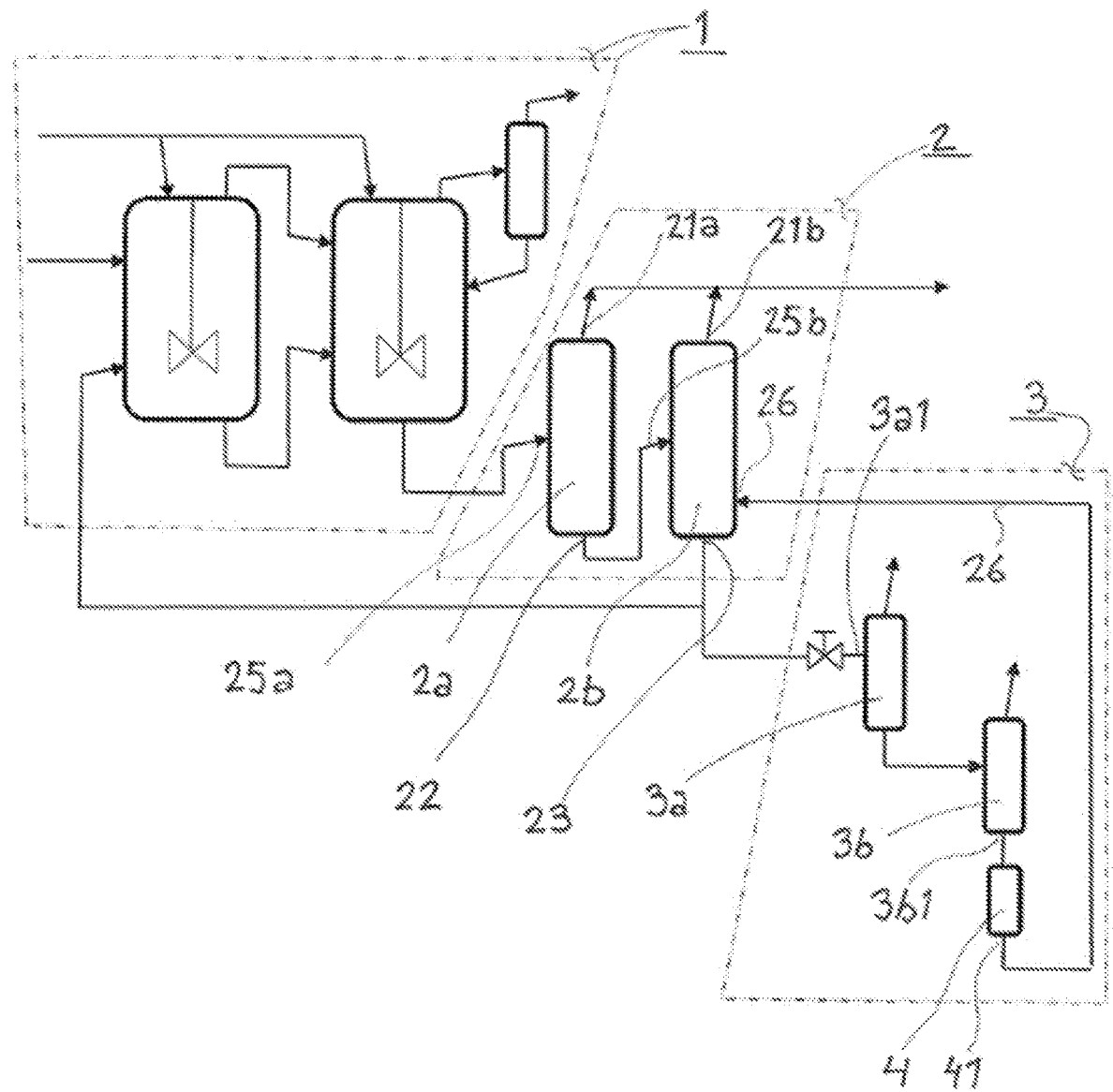
FIG. 1 illustrates a method for reducing heavy end formation and catalyst loss in a continuous hydroformylation process

Referring to the accompanying FIG. 1, the present invention refers to a method for reducing heavy end formation and catalyst loss in a continuous hydroformylation process, where an olefin or an olefin mixture is reacted with carbon monoxide and hydrogen in a reactor assembly (1) in the presence of a rhodium complex catalyst, comprising at least one organobisphosphite ligand, in order to produce an aldehyde. Said method comprises the following steps:

a) adding 0.01-1.5 wt % of an epoxide to the reaction mixture, b) separating the obtained aldehyde from a mixture of aldehyde, catalyst, ligand and early heavy ends in a distillation unit (2), c) separating early heavy ends by feeding a part of a catalyst and ligand return flow, comprising a mixture of catalyst, ligand, early heavy ends and rest aldehyde from a lower outlet (23) of a final stage (2*b*) of the distillation unit (2), into a short residence time evaporator unit (3) having at least a first rest aldehyde stripper stage (3*a*) and at least one last early heavy ends stripper stage (3*b*), said evaporator units (3) being of a falling film and/or wiped film type, the rest of the catalyst and ligand return flow being fed back to the reactor assembly (1), d) entering the catalyst and ligand mixture from a lower end (3*b*1) of the at least one last early heavy ends stripping stage (3*b*) into a cooling unit (4) immediately after stripping of early heavy ends.

In preferred embodiments of the present invention the formation of heavy ends is reduced by 10-80% at least 50%. That is a huge benefit for the economy of the hydroformylation process. The method of the present invention is a great way of using an epoxide, as an heavy ends inhibitor. Another benefit of the method according to the present invention is that the addition of epoxide increases the purity of the aldehyde product, without any other adjustments to the process.

Although the formation of heavy ends are limited by the addition of the epoxide, there are still heavy ends formed and over time they will gradually grow into even more high-boiling and complex heavy ends that are very difficult to separate from the reaction solution by distillation, since the phosphite ligand thermally decomposes at high temperatures. In the method of the present invention early heavy ends are separated and the catalyst and ligand are recovered and returned to the hydroformylation process. The term "early heavy ends" are to be understood as heavy ends that are possible to separate in an evaporator under conditions mild enough not to cause thermal degradation of the organophosphite ligand utilized. In embodiment examples of this invention temperatures at or below about 170° C. and vacuum at or below 3 mbar have been utilized.

Removal of early heavy ends has been mentioned in the prior art. EP404193 discloses a process for the rhodium-catalyzed hydroformylation of olefins to aldehydes, providing a means for recovering valuable components in gaseous streams by scrubbing the streams with a stripped or cooled catalyst solution. In this process set up there is an optional evaporator to remove heavy ends. This heavy end separation unit is however dimensioned to take care of the whole catalyst and ligand return flow, which requires a rather large and energy consuming evaporator with a residence time that risk substantial thermal breakdown of the ligand. Due to the reduced heavy end formation caused by the epoxide addition in the method according to the present invention, it has shown through calculations and process simulation to be sufficient to allow as little as below 10% or even 1% of the catalyst and ligand return flow to pass through a heavy end stripping stage in order to separate early heavy ends from the process. This allows for a smaller and more cost effective evaporation unit with shorter residence time and short path, which is a highly desired property in order not to cause thermal breakdown of the ligand. One consequence of the method of the present invention is an increased life span of the delicate organophosphite ligand.

The amount of epoxide used in accordance with the method of the present invention is an amount sufficient to interact with the acidic ligand decomposition products which cause formation of heavy end upon reaction with the aldehyde product. Preferably, the epoxide is added in an amount of 0.1-1 wt %, and most preferably 0.2-0.5 wt % of the reaction mixture. The epoxide is suitably selected from the group consisting of cyclohexene oxide, 2,3-epoxynorbornane, 1,2-octene oxide, 1,2-dodecene oxide, 1,2-cyclododecene oxide, 1,2-decene oxide, 1,2-hexadecene oxide, 1,2-octadecene oxide, 1,2-cyclododecene oxide, 1,2-epoxydodecane, 2,3-epoxybutane and 3,4-epoxycyclohexylmethyl-3,4-epoxycyclohexanecarboxylate. The epoxide is preferably a cycloaliphatic epoxide and most preferably the epoxide is 3,4-epoxycyclohexylmethyl-3,4-epoxycyclohexanecarboxylate.

According to one embodiment of the invention the distillation unit (2) have at least a first and a final stage (2a and 2b respectively) where all stages (2a and 2b respectively) have an upper outlet (21a and 21b respectively) for aldehyde, a central inlet (25a and 25b respectively) for the mixture of aldehyde, catalyst, ligand and early heavy ends and lower outlets (22 and 23 respectively) for the mixture of rest aldehyde, catalyst, ligand and early heavy ends. The separated distilled aldehyde product may then be condensed and recovered in any conventional manner.

The separation of early heavy ends in step c) is in accordance with one embodiment of the present invention performed discontinuously at regular intervals through means of analysis of heavy ends presence in the catalyst and ligand return flow. The analysis can be performed either manually or through automation.

The separation of early heavy ends in step c) can in accordance with another embodiment of the present invention be performed continuously. The continuous separation of early heavy ends can accordingly be guided through means of statistical process guiding, where analysis of heavy end presence in the catalyst and ligand return flow is regulating the flow through the evaporator unit (3) as well as at least the temperature in the early heavy ends stripper stage (3b).

In a preferred embodiment of the present invention 1-10% of the catalyst and ligand return flow is being fed into the evaporator unit (3) in step c) to separate early heavy ends.

The at least one last early heavy ends stripping stage (3b) suitably have a short path and is operated in the range 0.1-3 mbar and at a temperature in the range 130-170° C.

The cooling unit (4) have an outlet (41) through which the recovered, through the process purified, catalyst and ligand mixture is fed back to the reactor assembly (1).

According to one embodiment of the invention the recovered catalyst and ligand mixture from the outlet (41) of the cooling unit (4) is fed back to the reactor assembly (1) via a return inlet (26) of the final stage (2b) of the distillation unit (2).

The olefin in the method of the present invention is preferably a C2-C6 olefin, such as ethene, propene and/or butene. Most preferably the olefin is 1-butene and/or cis- or trans-2-butene, or a mixture thereof. The butene feed in the hydroformylation reaction of the method of the present invention comprises a maximum of 2 wt % isobutene.

Hydroformylation of mixed butene feeds containing 1-butene and cis- and trans-2-butene, will generate a mixture of n-valeraldehyde and 2-methyl butyraldehyde. The n/iso ratio is affected by the choice of ligand. The ligand used in combination with rhodium in the method of the present invention is an organobisphosphite ligand of Formula (I)

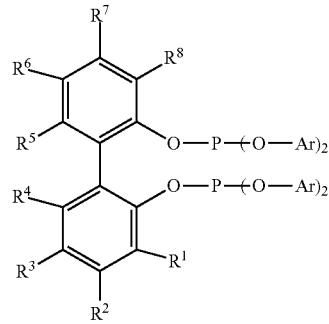

Formula (I)

wherein —$R^1$, —$R^2$, —$R^3$, —$R^4$, $R^5$, $R^6$, $R^7$ and $R^8$ individually is hydrogen or a linear or branched alkyl group and —Ar is a substituted or unsubstituted aryl group, such as a group of Formula (II) or (III).

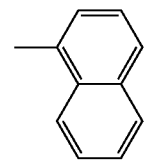

Formula (II)

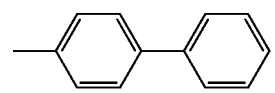

Formula (III)

In preferred embodiments of the present invention, —Ar is a group of Formula (II) and —$R^1$, —$R^3$, —$R^6$ and —$R^8$ are n-butyl, iso-butyl or tert-butyl. In a further preferred embodiment, —$R^4$ and —$R^5$ are methyl. Most preferably the ligand has the structure of formula (IV), having CAS no. 198979-98-5, hereinafter designated A4N3.

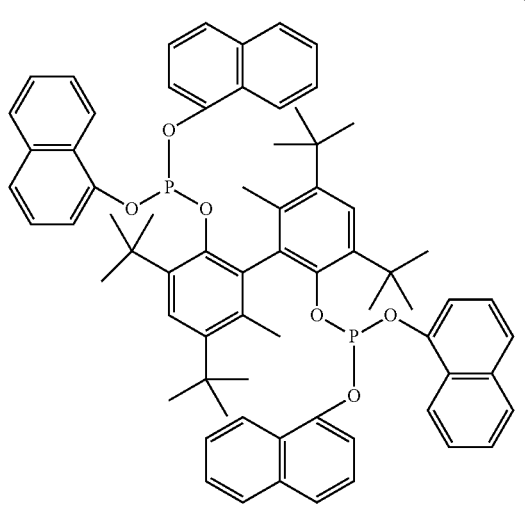

Formula (IV)

Said Formula (I) ligand is suitably used in an amount of 0.5-15 wt %, such as 1-10 wt % or 1-5 wt % calculated on total reaction mixture.

Due to the reduced amount of heavy ends formed in the hydroformylation process when using the method of the present invention, a reduced amount of water is present in the reaction mixture and the organobisphosphite ligand is hydrolyzed to a less extent. This allows for the time between partial or complete catalyst changes to be dramatically increased, i.e. provides a prolonged catalyst lifetime.

The continuous hydroformylation process of the method of the present invention is preferably conducted at a temperature in the range of 80° C. to 130° C., and at a total pressure of not more than about 20 bar. A continuous or periodic addition of epoxide to the reaction mixture will maintain a low level of epoxide in the reactor that will keep the heavy ends concentration at a manageable, steady level without autocatalytic degradation of the organobisphosphite ligand. An accurate amount of epoxide addition can be achieved by statistical process control. A device measuring the amount of unreacted epoxide, the amount of formed heavy ends, and/or the amount of acidic ligand decomposition products in the reaction mixture, can be used to calculate the necessary amount of epoxide addition in order to keep a concentration of about 0.5 wt %, preferably 0.1 wt %, epoxide in the reaction mixture.

In circumstances where the organobisphosphite ligand of Formula (I) risk exposure to oxygen, small amounts of one or more less efficient and/or cheaper tertiary phosphines as anti-oxidants can be added in order to avoid or substantially reduce oxidation of the ligand. The anti-oxidant is preferably added in an amount of 0.01-5, such as 0.05-2 wt % of the reaction mixture. Said anti-oxidant is preferably a tertiary phosphine, such as triarylphosphine, dicycloalkylarylphosphine and/or cycloalkyldiarylphosphine. Especially preferred anti-oxidants include, phenyldi(o-, m- or p-tolyl)phosphine, diphenyl(o-, m- or p-tolyl)phosphine, tri(o-, m- or p-tolyl)phosphine, phenyldibenyzylphosphine, diphenylbenzylphosphine, tribenzylphosphine, phenyldinaphthylphosphine, diphenylnaphthylphosphine, trinaphthylphosphine, dicyclohexyl-benzylphosphine and/or cyclohexyldibenzylphosphine.

Rhodium is suitably and advantageously present in the reaction mixture of the present invention in an amount of 20-1000, such as 50-550, ppm by weight of the reaction mixture and preferably charged in form of a precursor selected from the group consisting of a hydride, a halide, a nitrate, a carbonyl compound, an acetate and a dicarbonyl-acetylacetonate. In especially preferred embodiments of the method of the present invention, said precursor is selected from rhodium(III)nitrate, rhodium(III)acetate, rhodium(I)acetate, acetylacetonatedicarbonyl rhodium(I), di(rhodium) tetracarbonyl dichloride, dodecancarbonyltetrarhodium and/or hexadecane carbonylhexarhodium.

Solvents may be present in the reaction mixtures of the method of the present invention and are typically saturated hydrocarbons, aromatic hydrocarbons, ethers, aldehydes, ketones, nitriles and aldehyde condensation products. Suitable solvents are for instance pentanes, cyclohexane, benzene, xylene, toluene, diethyl ether, butyraldehyde, valeraldehyde, acetophenone, cyclohexanone and/or benzonitrile.

The following Examples further illustrate the method of the invention without limiting it in any way.

EXAMPLES

Example 1 illustrates a reduction in heavy ends formation, when the method of the present invention is applied to a hydroformylation reaction mixture in an industrial production plant.

Example 2 illustrates an increase in purity of the aldehyde product, when the method of the present invention is applied to a hydroformylation reaction mixture in an industrial production plant.

Example 3 illustrates the effect of the method of the present invention in a pilot scale, evidencing a reduction in the rate of heavy ends formation.

Example 4 is a comparative lab experiment that illustrates the effect of different amounts of epoxide addition to a hydroformylation reaction mixture, evidencing a reduction in heavy ends formation rate and a reduction in ligand hydrolysis.

Example 5 illustrates a heavy end analysis of a 6 months old catalyst and ligand mixture.

Example 6 illustrates an early heavy end separation according to the present invention.

The added epoxide in all of the examples is 3,4-epoxy-cyclohexylmethyl 3,4-epoxycyclohexanecarboxylate:

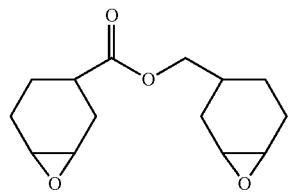 [SMILES: O=C(OCC1CCC2OC2C1)C1CCC2OC2C1]

Example 1

The amount of heavy ends removed, along with the aldehyde product, from an industrial hydroformylation process of the present invention was measured during a period of 8 months. During the first 5 months the amount of daily removed heavy ends gradually increased from about 2 tons to 5 tons. After 5 months an epoxide (3,4-epoxycyclohexylmethyl 3,4-epoxycyclohexanecarboxylate) was added to the reactor in an amount of 1 wt % of the reaction mixture. The epoxide was thereafter periodically added to the reactor in order to keep a concentration of about 0.5 wt % epoxide in the reaction mixture.

Figure 2:
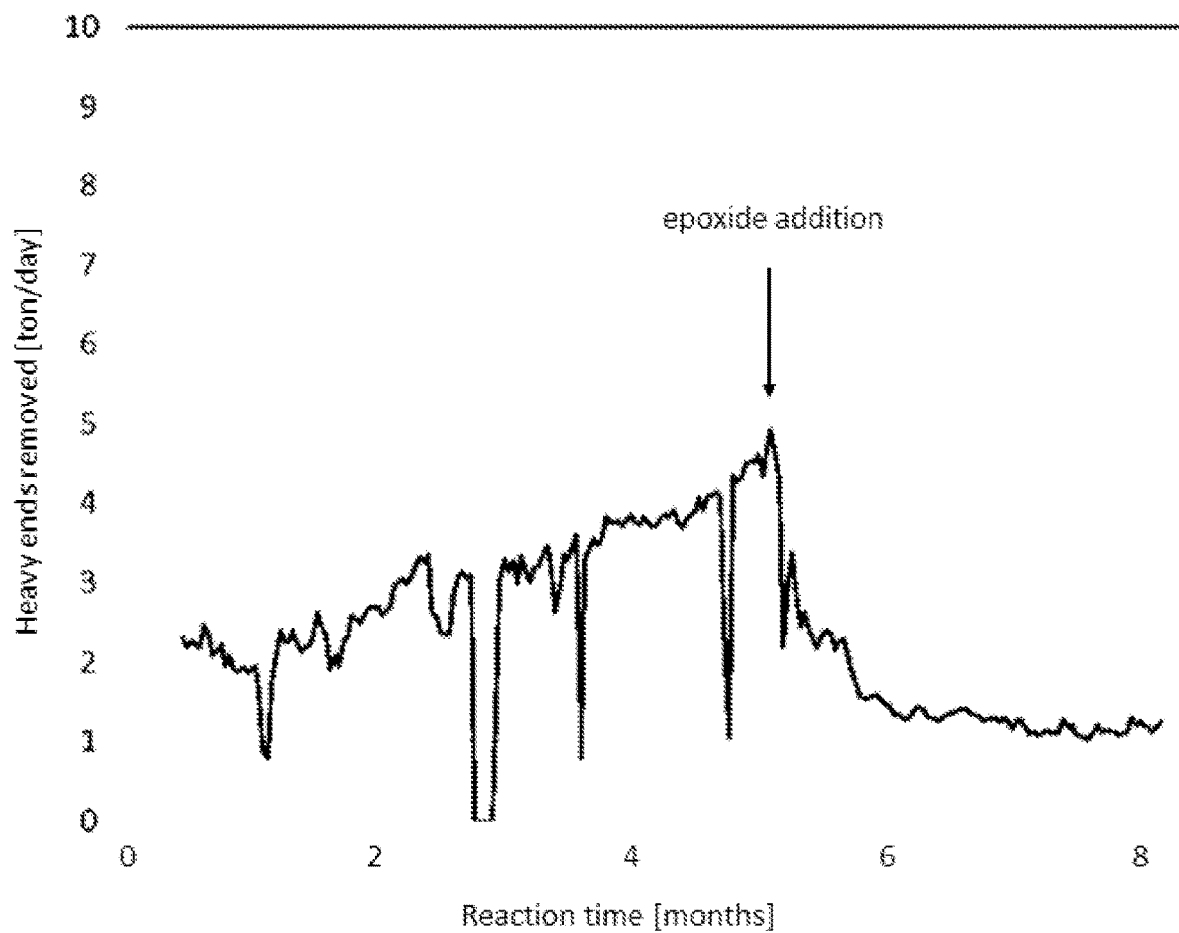
FIG. 2 is a graph showing a reduction of heavy ends upon addition of an epoxide to an industrial hydroformylation process.

The amount of heavy ends leaving with the product decreased drastically during the following month to a daily production level of 1 ton heavy ends, a 80% decrease in heavy ends formation. The result, evidencing a substantial reduction in heavy ends formation upon epoxide addition, is given in attached FIG. 2.

Example 2

The amount of aldehyde in the product stream from an industrial hydroformylation process of the present invention was measured during a period of 11 weeks. During the first 7 weeks the amount of valeraldehyde was below or about 98.5% of the content of the product stream. After 7 weeks the above-described epoxide was added to the reactor in an amount of 1 wt % of the reaction mixture. The epoxide was thereafter periodically added to the reactor in order to keep a concentration of about 0.5 wt % epoxide in the reaction mixture.

Figure 3:
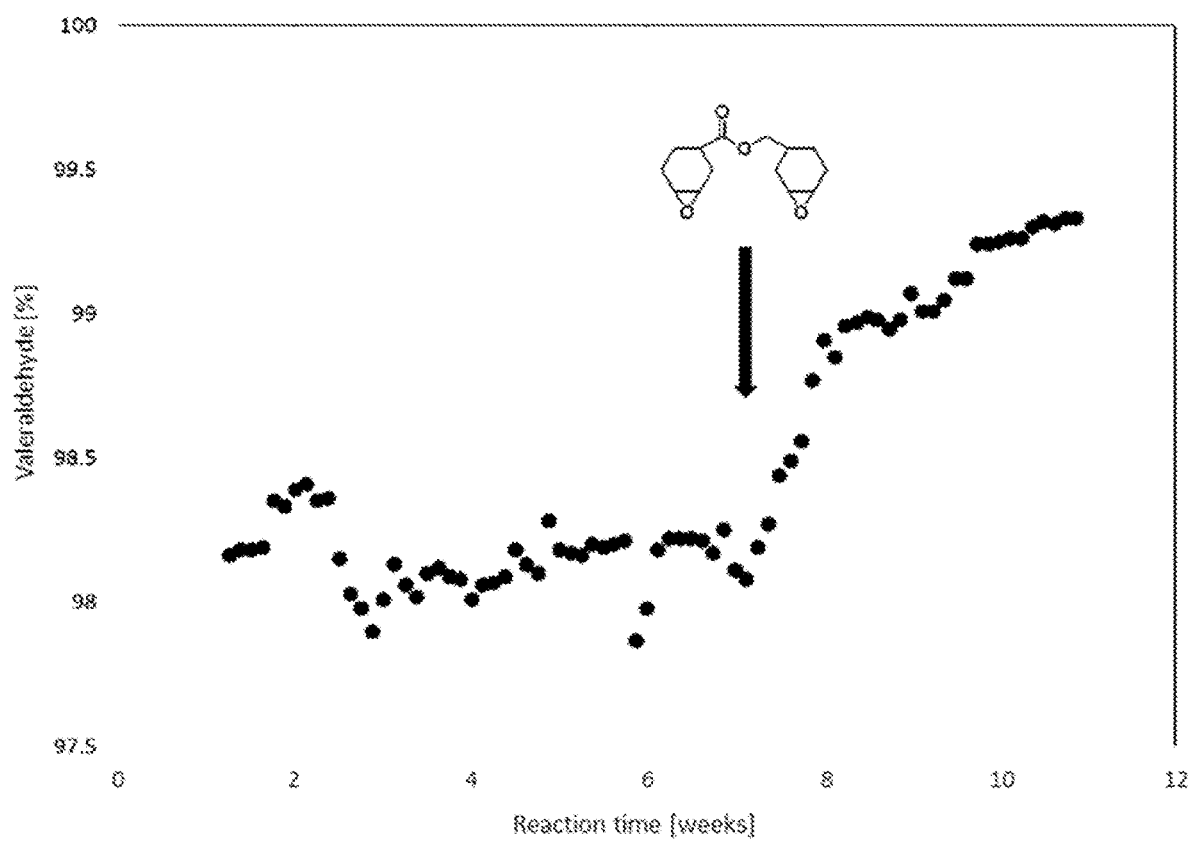
FIG. 3 is a graph showing an increase in purity of an aldehyde product upon addition of an epoxide to an industrial hydroformylation process.

The valeraldehyde content of the product stream steadily increased during the following 4 weeks to almost 99.5%, a 1% increase in purity, due to a dramatic decrease in more low-boiling heavy ends. The result, evidencing an increase in purity of the aldehyde product upon epoxide addition, is given in attached FIG. 3.

Example 3

Figure 4:
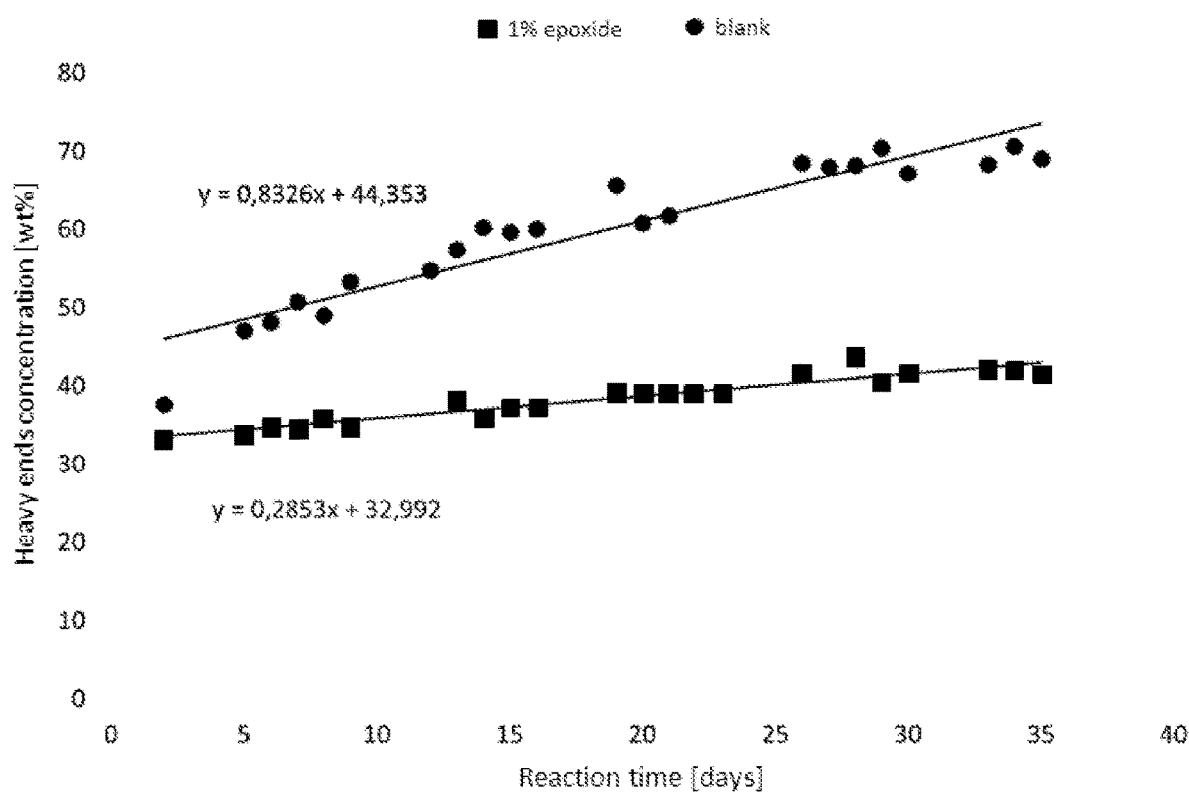
FIG. 4 is a graph showing a decline in the rate of heavy ends formation as analyzed by gas chromatography (GC) and high pressure liquid chromatography (HPLC)

Hydroformylation reactions were conducted for a period of 35 days in a continuous pilot scale process with two stirred tank reactors in series and a liquid recycle. An aged catalyst solution was taken from an industrial process and divided in two. One with an addition of roughly 1 wt % epoxide and the other one without any added epoxide. Samples of the reaction mixture were taken regularly and analyzed with gas chromatography (GC) and high pressure liquid chromatography (HPLC). The result of the analyses are given in attached FIG. 4, evidencing a clear decline in the rate of heavy ends formation. A reduction in the rate of heavy ends formation of up to 65%.

Example 4

Figure 5:
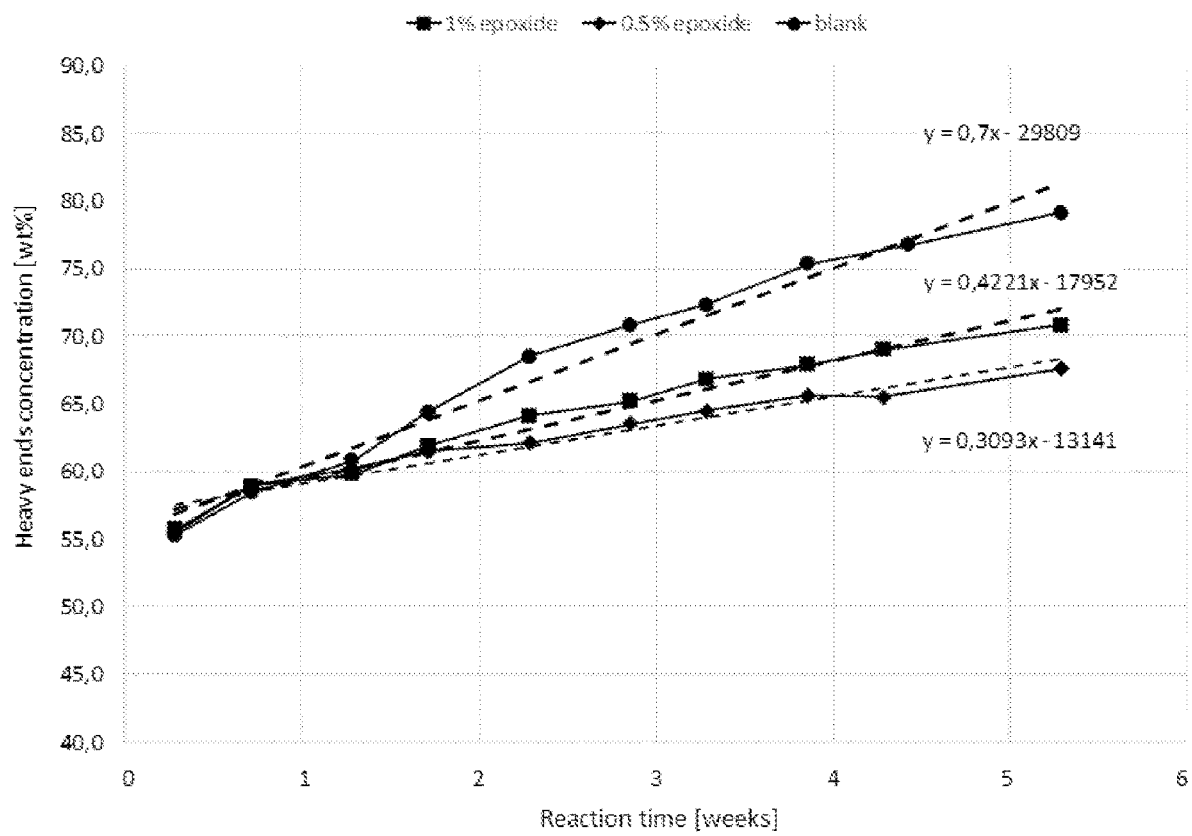
FIG. 5 is a graph showing a reduction heavy ends by addition of an epoxide to an industrial hydroformylation process.
Figure 6:
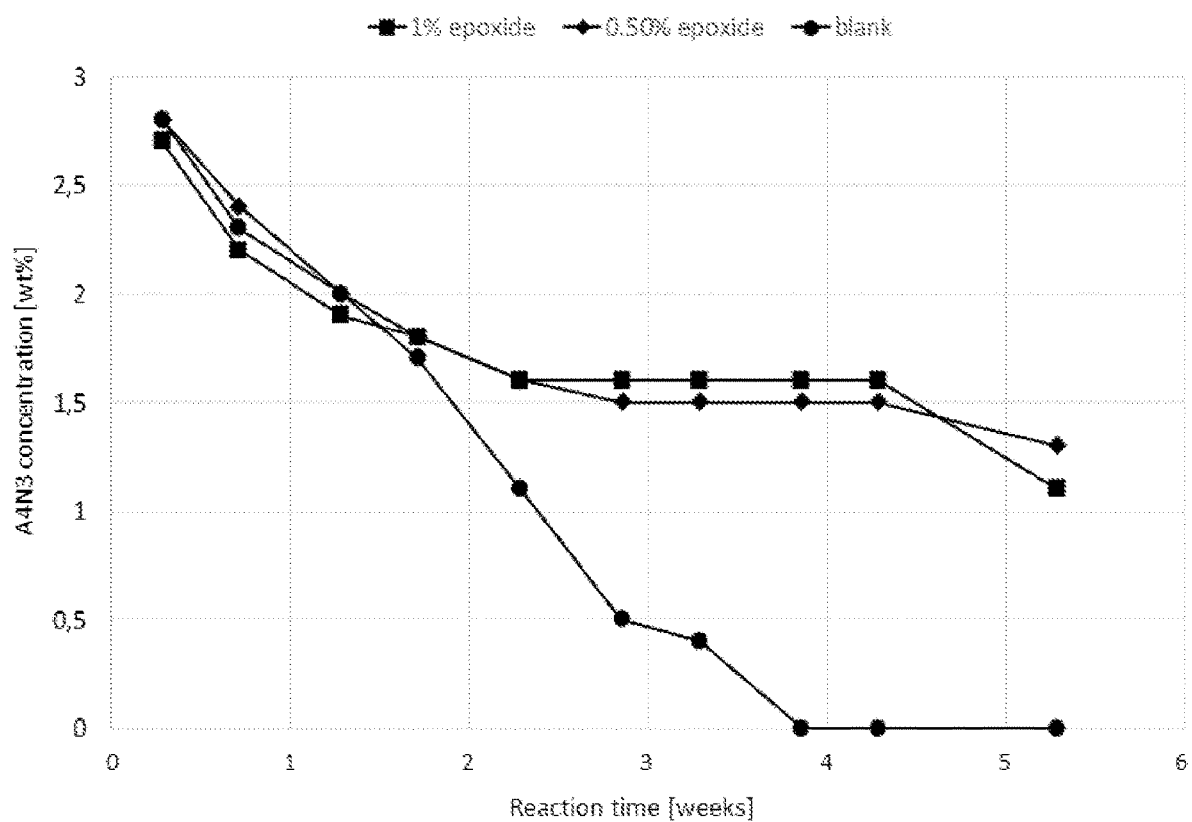
FIG. 6 is a graph showing a reduction in ligand hydrolysis by addition of an epoxide to an industrial hydroformylation process.

Three parallel experiments in lab scale were carried out to illustrate the present invention. An aged catalyst solution was taken from an industrial process and divided in three parts. The reactors were loaded with equal amounts of the reactor solution. In two of the reactors, epoxide was added to the reactor solution in amounts of 0.5 wt % and 1 wt %, respectively. The reactors were heated to 90° C. and pressurized with nitrogen to 14 bar and left for 5 weeks under stirring. Samples of the reaction mixture were taken at regular intervals and concentration of the compounds in the reaction mixture were determined from analysis of GC and HPLC. Obtained result is given in attached FIGS. 5 and 6, illustrating that the addition of an epoxide reduces the rate of heavy ends formation and reduces the ligand hydrolysis reaction, by scavenging the acidic ligand decomposition products. In closed systems with an aged catalyst solution, the addition of the epoxide decreases the heavy ends formation by 50% and the positive effect on the ligand stability is clearly visible.

Example 5

Catalyst and ligand mixture i.e. rhodium and bisphosphite ligand A4N3 (CAS 198979-98-5) which had been in use in a hydroformylation process for aldehyde production for longer than 6 months was analyzed in respect of heavy end content. Accordingly, the heavy end content did have ample time to build up through aldol condensation, Tischenko reaction, acetalization and oxidation as aldehydes produced in the hydroformylation process are highly reactive. The results from the analysis is presented in Table 1.

TABLE 1

| Heavy end [type] | Presence [wt %] |
| --- | --- |
| C5 | 5% |
| C10 | 5% |
| C15 | 25% |
| C20 | 16% |
| >C20 | 33% |
| >>C20 *) | 16% |

*) Heavy ends much heavier than C20 are difficult to analyze due to their complexity.

Example 6

Experiments were carried out in a laboratory set up, simulating continuous hydroformylation of 1-butene and syngas utilizing the catalyst and ligand mixture defined above. The aldehydes were distilled off in an evaporator and the heavy ends were separated from the remaining catalyst, ligand and heavy end mixture in a falling film evaporator with short residence time and short path. The pressures, temperature, amount of heavy ends separated is presented in Table 2.

TABLE 2

| Temperature [° C.] | Pressure [mbar] | C10 [wt %] | C15 [wt %] | C20 [wt %] | >C20 [wt %] | >>C20*) [wt %] |
| --- | --- | --- | --- | --- | --- | --- |
| 170 | 0.5 | 93 | 42 | 29 | 15 | 1 |
| 170 | 3.0 | 79 | 32 | 19 | 12 | 0 |
| 170 | 3.0 | 89 | 33 | 18 | 11 | 0 |

*)Heavy ends much heavier than C20 are difficult to analyze due to their complexity.

The results above show that the lighter heavy ends are easily separated from the catalyst and ligand mixture to a very high degree under these relatively mild conditions. It was observed that also lighter ligand degradation products were separated from the catalyst and ligand mixture. Such ligand degradation products are known to catalyse degradation of intact ligands. The herein described invention will accordingly not only decrease the formation of heavy ends and prevent loss of costly rhodium catalyst through bleeding out together with complex heavy ends, it will also increase the life span of the delicate organophosphite ligand. Due to radical reduction of complex heavy ends, interruptions in production will also be less occurring. The radical reduction of complex heavy ends is achieved by continuous or recurrent separation of the early heavy ends from the reaction/product solution stream as it takes from days, weeks or even months for the complex, >C20→>>C20, heavy ends to form, all depending on production parameters.

The invention claimed is:

1. A method for reducing heavy end formation and catalyst loss in a continuous hydroformylation process, where an olefin or olefin mixture is reacted with carbon monoxide and hydrogen in a reactor assembly (1) in the presence of a rhodium complex catalyst comprising at least one organobisphosphite ligand, in order to produce an aldehyde, the method comprising:
   a) adding 0.01-1.5 wt % of an epoxide to a reaction mixture,
   b) separating an obtained aldehyde from a mixture of aldehyde, catalyst, ligand, and early heavy ends in a distillation unit (2),
   c) separating early heavy ends by feeding a part of a catalyst and ligand return flow, comprising a mixture of catalyst, ligand, early heavy ends and residual aldehyde from a lower outlet (23) of a final stage (2b) of the distillation unit (2), into a short residence time evaporator unit (3) having at least a first residual aldehyde stripper stage (3a) and at least one last early heavy ends stripper stage (3b), the evaporator unit (3) being of a falling film and/or wiped film type, the rest of the catalyst and ligand return flow being fed back to the reactor assembly (1),
   d) entering the catalyst and ligand mixture from a lower end (3b1) of the at least one last early heavy ends stripping stage (3b) into a cooling unit (4) immediately after stripping of early heavy ends.

2. The method according to claim 1, wherein the epoxide is added in an amount of 0.1-1 wt % of the reaction mixture.

3. The method according to claim 1, wherein the epoxide is added in an amount of 0.2-0.5 wt % of the reaction mixture.

4. The method according to claim 1, wherein the epoxide is a cycloaliphatic epoxide.

5. The method according to claim 1, wherein the epoxide is chosen from cyclohexene oxide, 2,3-epoxynorbornane, 1,2-octene oxide, 1,2-dodecene oxide, 1,2-cyclododecene oxide, 1,2-decene oxide, 1,2-hexadecene oxide, 1,2-octadecene oxide, 1,2-cyclododecene oxide, 1,2-epoxydodecane, 2,3-epoxybutane and 3,4-epoxycyclohexylmethyl-3,4-epoxycyclohexanecarboxylate, and combinations thereof.

6. The method according to claim 1, wherein the epoxide is 3,4-epoxycyclohexylmethyl-3,4-epoxycyclohexanecarboxylate.

7. The method according to claim 1, wherein the distillation unit (2) has at least a first and a final stage (2a and 2b respectively) where all stages (2a and 2b respectively) have an upper outlet (21a and 21b respectively) for aldehyde, a central inlet (25a and 25b respectively) for the mixture of aldehyde, catalyst, ligand and early heavy ends and lower outlets (22 and 23 respectively) for the mixture of residual aldehyde, catalyst, ligand and early heavy ends.

8. The method according to claim 1, wherein separating early heavy ends in c) is performed discontinuously at regular intervals by analysis of heavy ends presence in the catalyst and ligand return flow.

9. The method according to claim 1, wherein separating early heavy ends in c) is performed continuously.

10. The method according to claim 9, wherein continuous separation of early heavy ends is guided by statistical process guiding, where analysis of heavy end presence in the catalyst and ligand return flow is regulating the flow through the evaporator unit (3) as well as at least the temperature in the early heavy ends stripper stage (3b).

11. The method according to claim 1, wherein 1-10% of the catalyst and ligand return flow is being fed into the evaporator unit (3) in c) to separate early heavy ends.

12. The method according to claim 1, wherein the at least one last early heavy ends stripping stage (3b) has a short path and is operated in the range 0.1-3 mbar and at a temperature in the range 130-170° C.

13. The method according to claim 1, wherein the cooling unit (4) has an outlet (41) through which a recovered catalyst and ligand mixture is fed back to the reactor assembly (1).

14. The method according to claim 13, wherein the recovered catalyst and ligand mixture from the outlet (41) of the cooling unit (4) is fed back to the reactor assembly (1) via a return inlet (26) of the final stage (2b) of the distillation unit (2).

15. The method according to claim 1, wherein the olefin is a C2-C6 olefin.

16. The method according to claim 1, wherein the olefin is 1-butene and/or cis- or trans-2-butene.

17. The method according to claim 1, wherein the ligand is an organobisphosphite ligand of Formula (I)

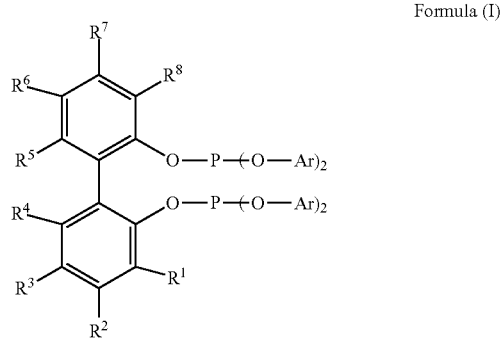

Formula (I)

wherein —$R^1$, —$R^2$, —$R^3$, —$R^4$, $R^5$, $R^6$, $R^7$ and $R^8$ are independently hydrogen or a linear or branched alkyl group and —Ar is a substituted or unsubstituted aryl group of Formula (II) or (III)

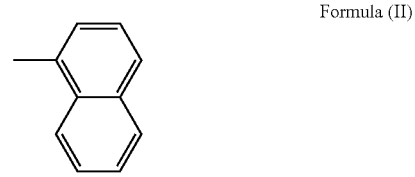

Formula (II)

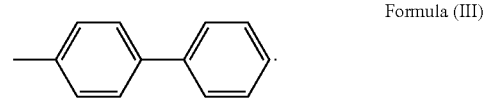

Formula (III)

18. The method according to claim 17, wherein —Ar is a group of Formula (II) and —$R^1$, —$R^3$, —$R^6$ and —$R^8$ are independently n-butyl, iso-butyl, or tert-butyl, and $R^4$ and $R^5$ are methyl.

19. The method according to claim 17, wherein the ligand has the structure of formula (IV):
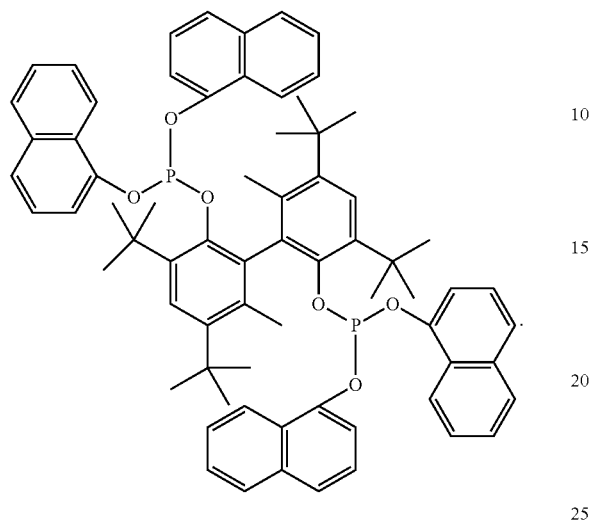
Formula (IV)
20. The method according to claim 1, wherein the ligand is present in an amount of 0.5-15 wt % of the reaction mixture.
* * * * *